April 18, 1972 E. C. CURTIS Plant Pat. 3,115
ROSE PLANT
Filed Feb. 24, 1970
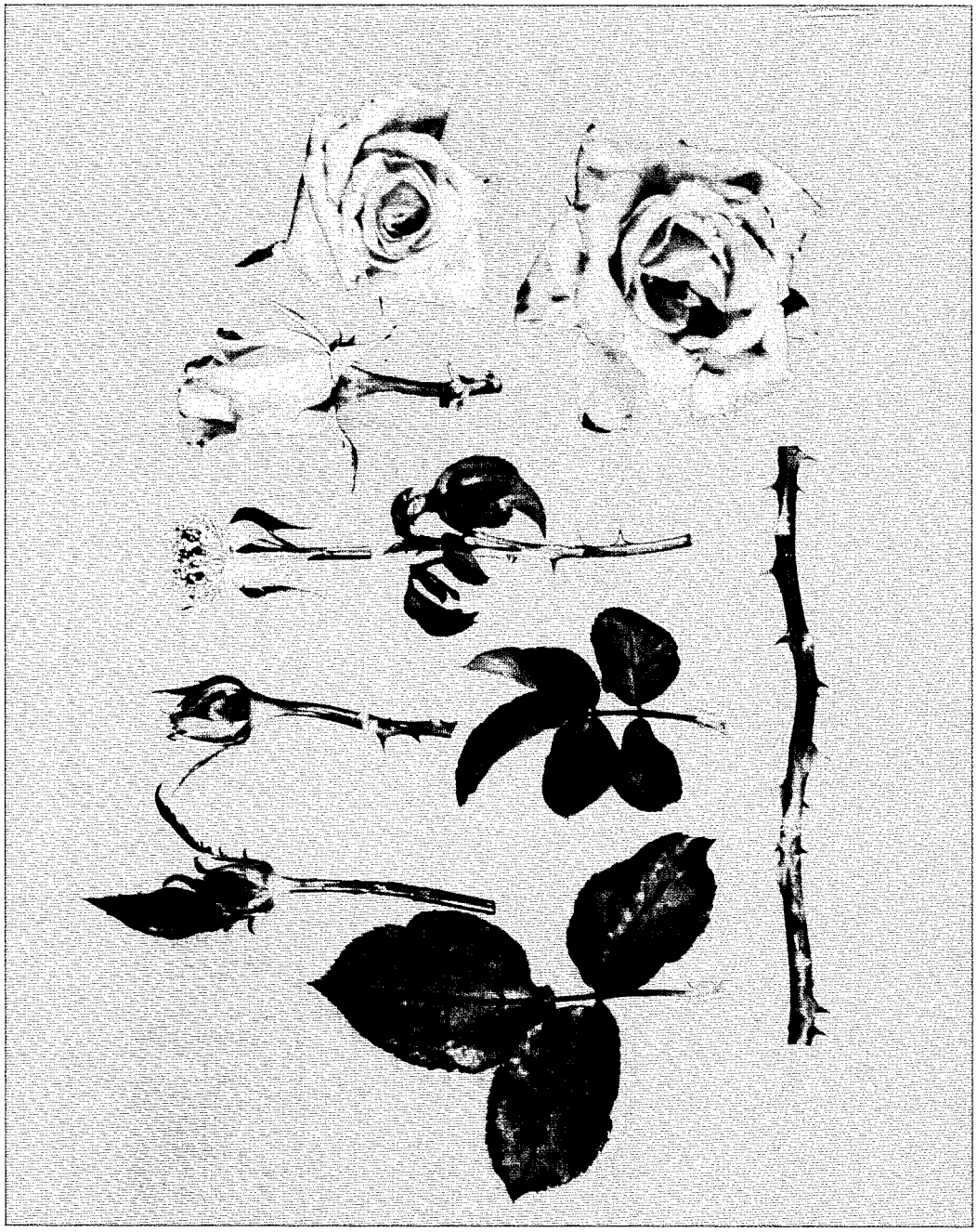

United States Patent Office

Plant Pat. 3,115
Patented Apr. 18, 1972

3,115
ROSE PLANT

Eldon C. Curtis, Dallas, Tex., assignor to
E. V. Kimbrew, Van Zandt County, Tex.

Filed Feb. 24, 1970, Ser. No. 13,868
Int. Cl. A01h *5/00*
U.S. Cl. Plt.—18 1 Claim

ABSTRACT OF THE DISCLOSURE

A new and distinct variety of hybrid tea rose plant produced by crossing Hawaii (Plant Patent No. 1,833) on Montezuma (Plant Patent No. 1,383).

The present invention relates to a new and distinct variety of rose plant of the hybrid tea class which was originated by crossing Hawaii (Plant Patent No. 1,833) on Montezuma (Plant Patent No. 1,383).

This rose differs from its pollen parent, Hawaii, (Plant Patent No. 1,833) by being more upright in growth with more and larger thorns. The foliage is more abundant and larger than the foliage of the seed parent, Hawaii.

This rose differs from its seed parent Montezuma (Plant Patent No. 1,383) by not growing as tall and being more upright in growth. The canes are larger with more and larger thorns. The foliage is also larger and darker green in color.

Essentially solid color, slightly more brilliant than the inner petal surface of the parent plants, the bloom is larger and more elongated.

The accompanying drawing shows typical specimens of the growth and habit of my new variety in different stages of development and in a color as nearly true as is possible to make the same in a color illustration of this character.

The following is a detailed description of my new rose variety with color terminology in accordance with the Horticultural Color Chart of the Royal Horticultural Society except where general color terms of ordinary dictionary significance are used:

Type: Upright bush, seedling, for garden decoration and cutflower use.
Class: Hybrid Tea.

*The flower*

Locality where grown: Canton, Tex.
Flowers borne: Singly with very few clusters; strong stems of good length.
Quality of bloom: Profuse.
Continuity: Throughout the growing season.
Fragrance: Mild rose.
Bud: Pointed bud.
- *Peduncle.*—Medium length, strong.
- *Before calyx breaks.*—Pointed. Size—medium. Form—pointed.
- *As calyx breaks.*—Ovoid form. Color—41B-Red to 46A-Red.
- *As first petal opens.*—Size—medium. Form—pointed. Color—orange-red class; outside—41B-Red to 46A-Red; inside—43A-Red. Opening—slow to open.

Bloom: Urn-shape.
- *Size when fully open.*—Medium; 3 to 4 inches, but larger in cool weather.
- *Petalage.*—30 to 35 petals, regularly arranged.
- *Form.*—Urn shape.

Petals:
- *Shape.*—*Outer*—rounded; seldom with point or indentation. Intermediate—rounded. Inner—rounded.

- *Color.*—Orange-red class. *Outer petal*—outside surface—41C-Red; inside surface—39C-Red. *Intermediate petal*—outside surface—41B-Red; inside surface—39C-Red. *Inner petal*—outside surface—41B-Red; inside surface—39C-Red.

This description was made from a rose that was open for three days, outdoors in October 1969, at Canton, Tex.

Color: Orange-red.
- *Outer petal.*—Outside surface—41 D-Red; inside surface—41 D-Red. *Inner petal*—outside surface—41D-Red; inside surface—39C-Red.
- *General color effect.*—Newly opened flower; Orange-red class (41C-Red). Three days open: Orange-red class (410-Red).
- *Behavior.*—Holds bud and flower form and color a a long time; very slow to open. Petals shed cleanly from plant.
- *Flower longevity.*—Two weeks in October.

*Reproductive organs*

Stamens: Medium, arranged regularly around pistils; many.
Filaments: Medium length. Color—44D-Red.
Anthers: Many, medium size. Color—12C-Yellow.
Pollen: Moderate, yellow (general color term).
Pistils: Many, medium in size.
Styles: Orange-red (44C-Red), uneven, loosely bunched.
Stigma: Yellow (21D-Yellow orange).
Ovaries: Many, enclosed in receptacle.
Hips: Few.
Sepals: Uniformly downward after buds begin to open.
Seeds: Twelve to fifteen per hip.

*Plant*

Foliage:
- *Leaves.*—Compound, 3 to 7 leaflets
- *Leaflets.*—Shape—Ovate with acute apex, finely serrated.
- *Color.*—Mature—upper surface—137B-Green; under surface—138B-Green.
- *Young.* — Upper surface — Greenish red (general color term). Under surface—Light greenish red (general color term).
- *Rachis (the supporting stem of the compound leaf).* — Upper side — smooth. Under side — few prickles.
- *Stipules.*—About ½ inch long; auricle about ⅛ inch long.
- *Disease.*—Average in disease resistance.

Growth:
- *Habit.*—Upright and nicely compact, each flower stem of good length and seldom in candelabra.
- *Growth.*—Vigorous.
- *Canes.*—Medium to heavy.
- *Main stems.*—Straight; good length for each flower stem. Color—Medium green (138B Green).
- *Prickles.*—Medium in number, relatively short and slanted downward. Color—Reddish brown (general term).
- *Hairs.*—Few to none. Color—Reddish brown (general term).
- *New Shoots.* — Reddish purple (general term). Color—Prominent due to reddish color (attractive).
- *Prickle*—medium in number, relatively short, slanted downward. Color—Reddish-purple (general term).
- *Hairs*—few to none. Color—Reddish-purple (general term).

I claim:

1. A new and distinct variety of rose plant of the hybrid tea class, substantially as herein shown and described, characterized particularly as to novelty by the combination of good growing and flower producing habits, medium to large flowers which are borne on strong stems of good length, good flower form, better than average disease resistance, attractive brilliant color corresponding to Orange-red (class 41C-Red), and good keeping qualities of flowers as cut flowers and also slow to open and flower longevity on plant.

No references cited.

ROBERT E. BAGWILL, Primary Examiner